United States Patent [19]
Peck et al.

[11] Patent Number: 6,086,905
[45] Date of Patent: Jul. 11, 2000

[54] TOPICAL COMPOSITIONS USEFUL AS SKIN PENETRATION BARRIERS

[76] Inventors: James V. Peck, 904 Wilaka Rd., Richmond, Va. 23227; Gevork Minaskanian, 11701 Lockport Ter., Richmond, Va. 23233; Jonathan Hadgraft, 36 Station Road, Penarth, S. Glenn, United Kingdom

[21] Appl. No.: 08/102,176

[22] Filed: Aug. 4, 1993

Related U.S. Application Data

[63] Continuation of application No. 07/673,016, Mar. 21, 1991, abandoned.

[51] Int. Cl.⁷ .................................................... A01N 25/32
[52] U.S. Cl. ........................... 424/406; 424/59; 424/70.9; 574/376
[58] Field of Search ........................... 424/406, DIG. 13, 424/59, 70.9; 574/222.2, 228.8, 274, 823, 974, 376

[56] References Cited

U.S. PATENT DOCUMENTS

| | | | |
|---|---|---|---|
| 3,100,180 | 8/1963 | Smith et al. | 167/91 |
| 4,960,771 | 10/1990 | Rajadhyaksha | 514/228.8 |
| 5,091,379 | 2/1992 | Aungst | 514/159 |

FOREIGN PATENT DOCUMENTS

| | | | |
|---|---|---|---|
| 9000407 | 1/1990 | WIPO | A61K 47/22 |

OTHER PUBLICATIONS

Brain, K.R. et al., Abstract of "Electrostatic Factors in the Activity of Penetration Enhancers," presented at the Third International Prediction of Percutaneous Penetration Conference held in La Grande Motte, Apr. 1993.

Bronaugh, R.L. et al., "Vehicle Effects on Percutaneous Absorption: in vivo and in vitro Comparisons with Human Skin," *British Journal of Dermatology* 115: 1–11 (1986).

Franz, T.J., "The Finite Dose Technique as a Valid in vitro Model for the Study of Percutaneous Absorption in Man," *Curr. Probl. Dermatol.* 7: 58–68 (1978).

Hadgraft, J. et al., "Investigations on the Percutaneous Absorption of the Antidepressant Rolipram in vitro and in vivo," *Pharmaceutical Research* 7(*12*) : 1307–1312 (1990).

Williams, D. G., "Mechanisms of Action of Penetration Enhancers," Ph.D. Thesis, University of Wales, 1991.

*Primary Examiner*—Neil Levy
*Attorney, Agent, or Firm*—Sterne, Kessler, Goldstein & Fox

[57] ABSTRACT

Methods for preventing the penetration of toxic chemicals through the stratum corneum of the skin of a mammal are disclosed which employ, as a penetration prevention agent, at least one compound selected from the group consisting of compounds represented by the formula:

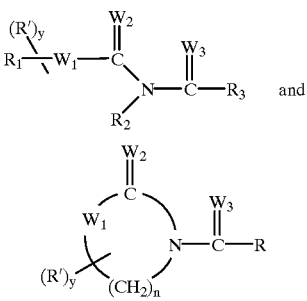

wherein $W_1$ is a divalent oxygen, sulfur or nitrogen radical, $W_2$ and $W_3$ are independently a divalent oxygen or sulfur radical, R' is an alkyl radical comprising from 1 to 4 carbon atoms, y is 0 or 1, $R_1$ and $R_2$ are alkyl radicals comprising from 1 to 10 carbon atoms and R and $R_3$ are individually a hydrocarbyl radical containing from 1 to 20 carbon atoms or a heteroatom-substituted derivative thereof wherein at least one but not two adjacent carbon atoms may be replaced by a divalent oxygen or sulfur radical or by NR", wherein R" is hydrogen or R', n is an integer from 2 to 5 and compounds represented by the above formula in which the ring and/or R includes one to three carbon carbon double bonds.

4 Claims, 2 Drawing Sheets

TOPICAL COMPOSITIONS USEFUL AS SKIN PENETRATION BARRIERS

BACKGROUND OF THE INVENTION

This application is a continuation of 07/673,016, filed Mar. 21, 1991, now ABD.

FIELD OF THE INVENTION

The invention relates to topical compositions useful for applying to the skin of a mammal, e.g., a human, to prevent the passage of toxic chemicals and other bioactive agents from the outside environment into the body, e.g., the bloodstream, or from the body into the outside environment. These topical compositions thus form skin penetration barriers.

SUMMARY OF THE ART

It is well known that the skin is an effective barrier to penetration to many chemical agents. The epidermis of the skin has an exterior layer of dead cells called the stratum corneum which is tightly compacted and oily and which provides an effective barrier against gaseous, solid or liquid chemical agents, whether used alone or in water or oil solutions. If an agent penetrates the stratum corneum, it can readily pass through the basal layer of the epidermis and into the dermis. If the agent is harmful, e.g., a toxic chemical, penetration of the stratum corneum is an event to be prevented.

Although the effectiveness of the stratum corneum as a barrier provides great protection, it also frustrates efforts to apply beneficial agents directly to local areas of the body. The inability of physiologically active agents to penetrate the stratum corneum has resulted in a great deal of research on penetration-enhancing agents for the skin. See for example U.S. Pat. Nos. 3,989,815; 3,989,816; 3,991,203; 4,122,170; 4,316,893; 4,405,616; 4,415,563; 4,423,040; 4,424,210; and 4,444,762. In contrast, there has been very little research carried out on chemical agents to prevent the penetration of toxic chemicals through the skin of mammals.

It is an object of this invention to provide new penetration prevention agents having the desirable property of blocking the percutaneous absorption of toxic chemicals and other harmful agents.

It is also an object to provide topical compositions for providing a barrier for the skin of a mammal to prevent the passage of bioactive agents in either direction through the skin.

Other objects and advantages of the instant invention will be apparent from a careful reading of the specification below.

In this description, the term "mammal" includes human beings and other forms of animal life, especially domesticated animals and pets.

SUMMARY OF THE INVENTION

This invention relates to topical compositions useful for providing a barrier for the skin of a mammal to prevent the passage of bioactive agents through the skin. More specifically, the invention relates to compositions useful for preventing the penetration of toxic chemicals through the skin of a mammal which comprises, as a penetration prevention agent, at least one compound selected from the group consisting of compounds represented by the formula:

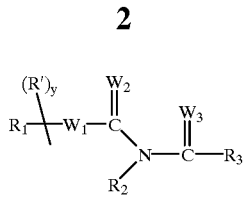

wherein $W_1$ is a divalent oxygen, sulfur or nitrogen radical, $W_2$ and $W_3$ are independently a divalent oxygen or sulfur radical, R' is an alkyl radical comprising from 1 to 4 carbon atoms, y is 0 or 1, $R_1$, $R_2$ are alkyl radicals comprising from 1 to 10 carbon atoms and $R_3$ is a hydrocarbyl radical containing from 1 to 20 carbon atoms or a heteroatom-substituted derivative thereof wherein at least one but not two adjacent carbon atoms may be replaced by a divalent oxygen or sulfur radical or by NR", wherein R" is hydrogen or R'. $R_1$ and $R_2$ may form a cyclic structure wherein $R_1$ and $R_2$ together may comprise 2 to 5 carbon atoms.

More particularly, the penetration enhancer in accordance with the present invention comprises one compound selected from the group consisting of compounds represented by the formula:

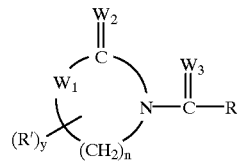

wherein $W_1$ is a divalent oxygen, sulfur or nitrogen radical, $W_2$ and $W_3$ are independently a divalent oxygen or sulfur radical, y is 0 or 1, n is an integer from 2 to 5, R is a hydrocarbyl radical containing from 1 to 20 carbon atoms or a heteroatom-substituted derivative thereof wherein at least one but not two adjacent carbon atoms may be replaced by a divalent oxygen or sulfur radical or by NR", wherein R" is hydrogen or R', and R' is an alkyl radical comprising from 1 to 4 carbon atoms and compounds represented by the above formula in which the ring and/or R includes one to three carbon-carbon double bonds.

Preferably all of the carbon-carbon bonds in the ring are saturated and even more preferably all of the carbon—carbon bonds in the compounds represented by the above formula are saturated bonds.

Preferably n is an integer of 2 to 4, e.g. 2.

Preferably R is a straight or branched chain alkyl radical having from about 1 to about 20 carbon atoms, more preferably a straight chain alkyl radical, e.g. a straight chain alkyl radical having from 6 to 20 carbon atoms.

The invention also provides a method for preventing the penetration of toxic chemicals through the skin of a mammal which comprises applying to the skin a topical composition which comprises, as a penetration prevention agent, one or more of the compounds represented by the above formula.

BRIEF DESCRIPTION OF THE DRAWINGS

The present invention can be more readily understood by a consideration of the following detailed description when taken in conjunction with the accompanying drawings, in which.

DETAILED DESCRIPTION OF THE INVENTION

Figure 1:
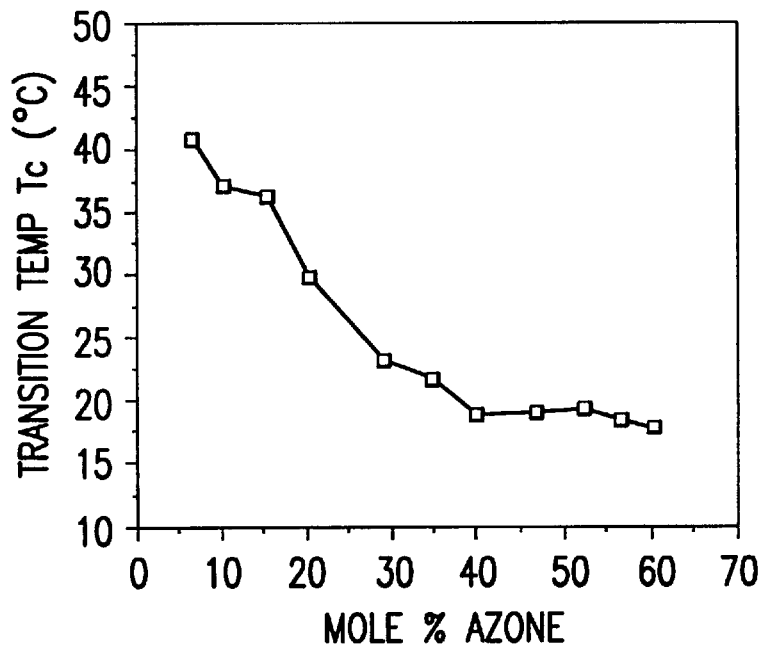
FIG. 1 is a plot of the effect of Azone® on the transition temperature of DL-α-dipalmitoylphosphatidyl choline (DPPC) liposomes.

The compounds represented by the above formula and useful as penetration prevention agents in the topical compositions of this invention may be made by the methods described below. Typical examples of compounds represented by the above formula include:

N-Dodecanoyl-2-oxazolidone
N-Decanoyl-2-oxazolidone
N-Octanoyl-2-oxazolidone
N-Octanoyl-2-thiazolidone
N-Acetyl-2-oxazolidone
N-Myristoleyl-2-oxazolidone
N-Undecylenyl-2-oxazolidone
N-(3-Ethylvaleryl)-2-oxazolidone
N-Dodecanoyl-tetrahydro-2H-1,3-oxazin-2-one
N-Dodecanoyl-tetrahydro-2H-1,3-thiazin-2-one
N-Dodecanoyl-tetrahydro-2H-1,3-oxazin-2-thione
N-Octanoyl-tetrahydro-2H-1,3-oxazin-2-one
N-Acetyl-tetrahydro-2H-1,3-oxazin-2-one
N-Myristoleyl-tetrahydro-2H-1,3-oxazin-2-one
N-Undecylenyl-tetrahydro-2H-1,3-oxazin-2-one
N-(3-Ethylvaleryl)-tetrahydro-2H-1,3-oxazin-2-one
N-Dodecanoyl-tetrahydro-1,3-oxazepin-2(3H)-one
N-Dodecanoyl-tetrahydro-1,3-oxazepin-2(3H)-thione
N-Decanoyl-tetrahydro-1,3-oxazepin-2(3H)-one
N-Decanoyl-tetrahydro-1,3-thiazepin-2(3H)-one
N-Decanoyl-tetrahydro-1,3-oxazepin-2(3H)-one
N-octanoyl-tetrahydro-1,3-oxazepin-2(3H)-one
N-Acetyl-tetrahydro-1,3-oxazepin-2(3H)-one
N-Myristoleyl-tetrahydro-1,3-oxazepin-2(3H)-one
N-Undecylenyl-tetrahydro-1,3-oxazepin-2(3H)-one
N-(3-Ethylvaleryl)-tetrahydro-1,3-oxazepin-2(3H)-one
N-Dodecanoyl-2-imidazolidone
N-Decanoyl-2-imidazolidone
N-Octanoyl-2-imidazolidone
1-Dodecanoyl-1,3-dimethylurea
1-Decanoyl-1,3-dimethylurea
1-Dodecanoyl,1-methyl-3-ethylurea The above penetration prevention agents may be formulated into topical compositions which, when applied to the skin of a mammal, e.g., a human, will function as barriers to the passage of bioactive compounds and agents through the skin in either or both directions. That is, the barrier may prevent the passage of toxic chemicals from the environment through the skin into the bloodstream or underlying tissues and/or organs of the mammal. This utility is especially desirable to prevent certain individuals from being exposed to toxic chemicals; e.g., farmers dealing with pesticides, workers cleaning up toxic waste spills, soldiers exposed to chemical weapons, etc. The barrier may also function to prevent allergic reactions to skin products such as cosmetics, sunburn preparations, etc., wherein it is desired to maintain the skin product ingredients on the surface of the skin. Additionally, the barrier may function to maintain drugs utilized to treat skin conditions on the skin surface.

(For the purpose of defining this invention, the term "bioactive agent" shall mean any compound, capable of passage through the skin or other membrane of a mammal, having any biological effect on the mammal. The biological effect may be either desirable or undesirable.)

Dosage forms for topical application may include solution nasal sprays, lotions, ointments, creams, gels, suppositories, sprays, aerosols and the like. Typical inert carriers which make up the foregoing dosage forms include water, acetone, isopropyl alcohol, freon, ethyl alcohol, polyvinylpyrrolidone, propylene glycol, fragrances, gel-producing materials, mineral oil, stearyl alcohol, stearic acid, spermaceti, sorbitan monooleate, "Polysorbates", sorbitol, methyl cellulose, etc.

The amount of the composition, and thus of the penetration prevent agent therein, to be administered will obviously be an effective amount for the desired result expected therefrom. This, of course, will be ascertained by the ordinary skill of the practitioner.

In general, the topical compositions of this invention may comprise from approximately 0.1 to 90 percent, by weight, of one or more of the compounds of the formula, preferably from approximately 1% to approximately 10%, and more preferably about 1% to about 5% of said compounds.

The invention is further illustrated by the following examples which are illustrative of various aspects of the invention and are not intended to limit the scope of the invention as defined by the appended claims.

EXAMPLE 1

Preparation of N-Dodecanoyl-2-oxazolidone 5 gm (0.0574 mole) 2-oxazolidone was partially dissolved with heating in 100 ml toluene. 24 ml (0.172 mole) triethylamine was added to the stirred mixture. Via dropping funnel 17.26 ml (0.0746 mole) lauroyl chloride was added. This mixture was then stirred 0.5 hour at room temperature. The reaction mixture was then filtered and the filtrate concentrated. The concentrate was dissolved in dichloromethane and this solution shaken with saturated aqueous sodium bicarbonate. The organic phase was dried over magnesium sulfate, filtered, concentrated and placed under high vacuum. Upon complete drying, the residue was triturated with petroleum ether and the solvent decanted off. The residue was purified by flash chromatography, employing ethyl acetate/petroleum ether as the eluant. The yield was 8.45 gm (55%) of a white solid with a melting point of 63–65° C.

EXAMPLE 2

Preparation of N-Decanoyl-2-oxazolidone

This compound was prepared following the procedure of Example 1 where decanoyl chloride was used in place of lauroyl chloride.

EXAMPLE 3

Preparation of N-Octanoyl-2-oxazolidone

This compound was prepared following the procedure of Example 1 wherein octanoyl chloride was used in place of lauroyl chloride.

EXAMPLE 4

Preparation-of N-Acetyl-2-oxazolidone

This compound was prepared following the procedure of Example 1 wherein acetyl chloride was used in place of lauroyl chloride.

EXAMPLE 5

Preparation of N-Myristoleyl-2-oxazolidone

This compound was prepared following the procedure of Example 1 wherein myristoleyl chloride was used in place of lauroyl chloride.

EXAMPLE 6

Preparation of N-(3-Ethyl-3-valeryl)-2-oxazolidone

This compound wars prepared following the procedure of Example 1 wherein 3-ethyl-3-valeryl chloride was used in place of lauroyl chloride.

EXAMPLE 7

Preparation of N-Dodecanoyl-tetrahydro-2H-1,3-oxazin-2-one

This compound was prepared following the procedure of Example 1 wherein tetrahydro-2H-1,3-oxazin-2-one was used in place of 2-oxazolidone.

EXAMPLE 8

Preparation of N-octanoyl-tetrahydro-2H-1,3-oxazin-2-one

This compound was prepared following the procedure of Example 1 wherein tetrahydro-2H-1,3-oxazin-2-one was used in place of 2-oxazolidone and octanoyl chloride was used in the place of lauroyl chloride.

EXAMPLE 9

Preparation of N-Dodecanoyl-tetrahydro-1,3-oxazepin-2(3H)-one

This compound was prepared following the procedure of Example 1 wherein tetrahydro-1,3-oxazepin-2(3H)-one was used in place of 2-oxazolidone.

EXAMPLE 10

Preparation of N-Decanoyl-tetrahydro-1,3-oxazepin-2(3H)-one

This compound was prepared following the procedure of Example 1 wherein tetrahydro-1,3-oxazepin-2(3H)-one was used in place of lauroyl chloride.

EXAMPLE 11

Preparation of N-Dodecanoyl-2-imidazolidone

To a solution of 2-imidazolidone in toluene with an appropriate base (e.g., triethylamine) is added a solution of an equimolar amount of lauroyl chloride in toluene. This is stirred overnight, filtered and the filtrate concentrated to give the above product.

EXAMPLE 12

Preparation of 1-Dodecanoyl-1,3-dimethylurea

To a solution of 1,3-dimethylurea in toluene with an appropriate base (e.g., triethylamine) is added an equimolar amount of lauroyl chloride. This is stirred overnight, filtered and concentrated to give the above product.

EXAMPLE 13

Liposomes are artificial vesicles, formed from a variety of substances such as phospholipids, which arrange themselves in aqueous solution to form bilayers. The physical state of the lipid bilayer membrane is an important property of the liposomes, particularly at the transition temperature, $T_c$, where the physical state of the phospholipid can change from a solid "gel-like" state to a fluid "liquid-crystalline" state in which the acetylated chains have some freedom of movement. While not wishing to be bound by theory, these phospholipids can serve as a model of intercellular skin lipids. Substances which increase the disarray of lipid bilayers, thereby lowering the transition temperature ($T_c$) have been shown to increase skin penetration of chemical agents. In contrast, it is thought that substances which increase the stability of lipid bilayers (increasing $T_c$) would act to minimize or prevent skin penetration of chemical agents.

The liposomes were prepared from a phospholipid, DPCC, and have a characteristic transition temperature ($T_c$) at 41.0 to 41.5° C. The influences of a penetration prevention agent and a penetration enhancer on the DPCC liposomes were measured, as follows:

1 mg of the phospholipid, along with the desired quantity of a penetration enhancer or a penetration agent, was dissolved in chloroform in a 10 ml glass round-bottomed flask. The chloroform was removed on a rotary film evaporator to leave a thin lipid film in the flask. To this film, 1 ml of deionized water was added, and the flask shaken vigorously for 5–10 minutes. The flask was then transferred to a shaking water bath, heated at 60° C., and incubated overnight to fully hydrate the lipid.

To scan the samples, 2 ml of deionized water was added to each flask, and the suspensions cooled in an ice bath. The chilled suspensions were then loaded into stirred, jacketed cuvettes and the absorbance measured at 500 nm.

Water pumped through the cuvette jackets provides a 0.15° C./sec. temperature increase of the suspensions.

Sharp changes in turbidity occur at the $T_c$ of a liposomal suspension, and as the temperature within the cuvette increases, a sharp drop in the absorbance indicates the $T_c$. This is then measured as being the intersection of tangents to the absorbance/temperature curve before, and after, the absorbance drop.

Figure 2:
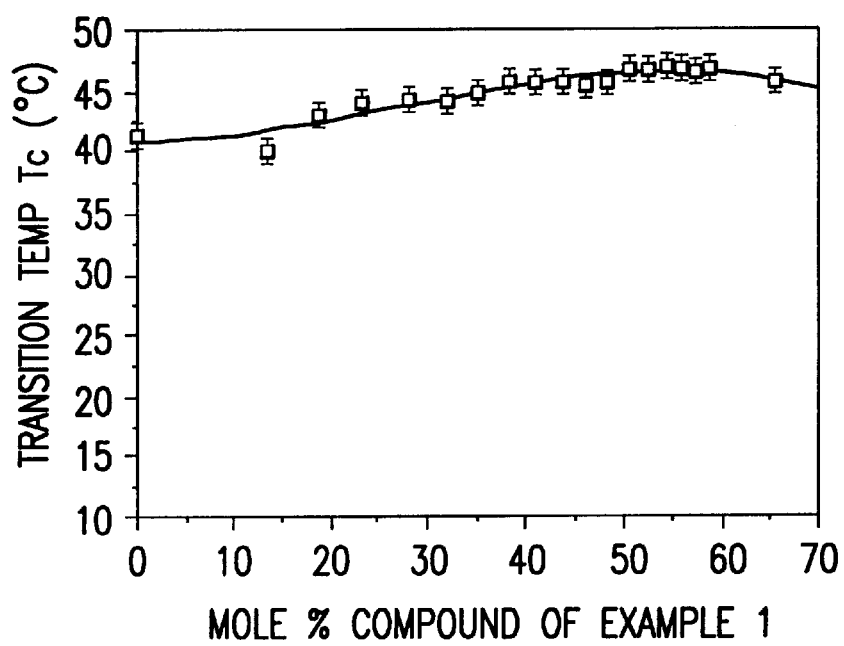
FIG. 2 is a plot of the effect of the compound of Example 1 on the transition temperature of DPPC liposomes.

As shown in FIG. 1, 1-N-dodecylazacycloheptan-2-one (Azone®), a known penetration enhancer, lowered the $T_c$ in a dose-responsive manner. In contrast, FIG. 2 shows that the compound of Example 1 increased the $T_c$ of the phospholipid layer.

It will be appreciated that the above method may enable one skilled in the art to determine which of the penetration prevention agents of the formula may be selected to prevent the penetration of a specific bioactive agent by carrying out the above measurement of $T_c$ in the presence of both the penetration prevention agent and the bioactive agent.

EXAMPLE 14

Metronidazole(2-(2-methyl-5-nitroimidazol-1-yl) ethanol) is used in the treatment of trichomoniasis and amoebiasis and in the prophylaxis and treatment of anaerobic infections. It is also used in the treatment of Crohn's disease—a debilitating enteritis.

Metronidazole was used in this sample as a model to investigate the prevention of transdermal delivery of various chemical agents as compared to penetration enhancers which promote the transdermal penetration of pharmacologically-active agents.

Strips of female Caucasian skin (approximate size 12 cm×5 cm) were obtained post mortem from the abdominal region. Donor age varied between 50 and 83 years old. The samples were relatively hairless.

The subcutaneous fat was removed from the sample by blunt dissection using a scalpel and scissors, taking care not to cut into the dermis. The full thickness skin was either used immediately or stored flat in an evacuated plastic bag at 4° C. in a freezer for up to two weeks prior to use.

The skin samples were then cut to the appropriate size and clamped, dermal side downwards, between the ground glass faces of a volume calibrated Franz-type diffusion cell. In this Franz-type cell, the passage of drug from the stratum corneum side of the membrane to the receptor fluid was monitored by sampling at regular intervals from the receptor port.

The area of the skin exposed after clamping in the cell was 0.5 cm$^2$. The receptor compartment was filled with freshly prepared iso-osmotic phosphate-buffered saline at a pH of 7.4, containing 0.01% w/v phenylmercuric nitrate as a preservative. The receptor phase was degassed prior to use to prevent the formation of air bubbles under the dermis, and the receptor fluid stirred with a magnetic flea to minimize any formation of stagnant layers. The receptor compartment was maintained at 37° C. in a thermostatted water bath, and the donor compartment at ambient laboratory temperature. The temperature of the skin surface was around 30° C. (±2° C.).

The skin and the receptor solution were then left to equilibrate for one hour prior to any pretreatment. If any air bubbles formed under the dermis, they were removed by gently rocking the cell. After one hour, the skin was pretreated with either (a) 50 μl ethanol as the control or (b) 50 μl of a 1% ethanolic solution of the penetration prevention agent or the penetration enhancer under study.

After pretreatment, the cells were left for two hours to allow evaporation of the applied ethanolic solutions. The donor compartments were then loaded with 100 μl of a 5 μmol/ml solution of metronidazole in ethanol. At appropriate intervals, 0.5 ml of the receptor solution were removed for analysis and replaced with an equivalent volume of iso-osmotic buffer which was pre-thermostatted to 37° C.

Each experiment was performed in quadruplicate with skin taken from the same donor. Permeation was studied over a period of 48 hours. The results are shown in FIGS. 3 and 4.

Figure 3:
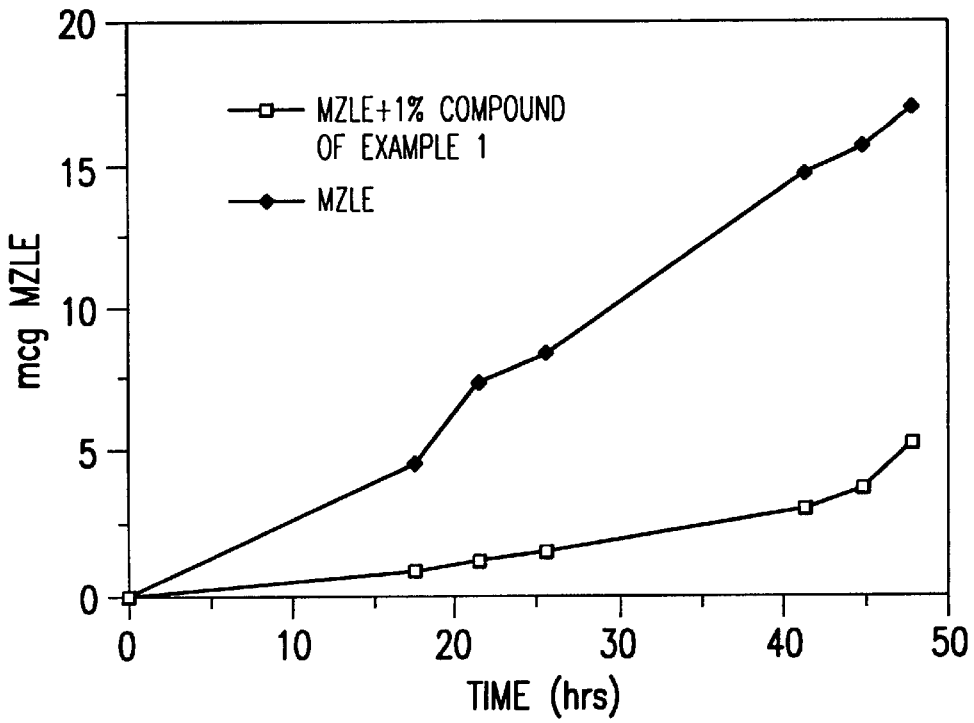
FIG. 3 is a plot of metronidazole (MZLE) penetration through female Caucasian skin samples as a function of time and showing the effect of the compound of Example 1 on penetration.
Figure 4:
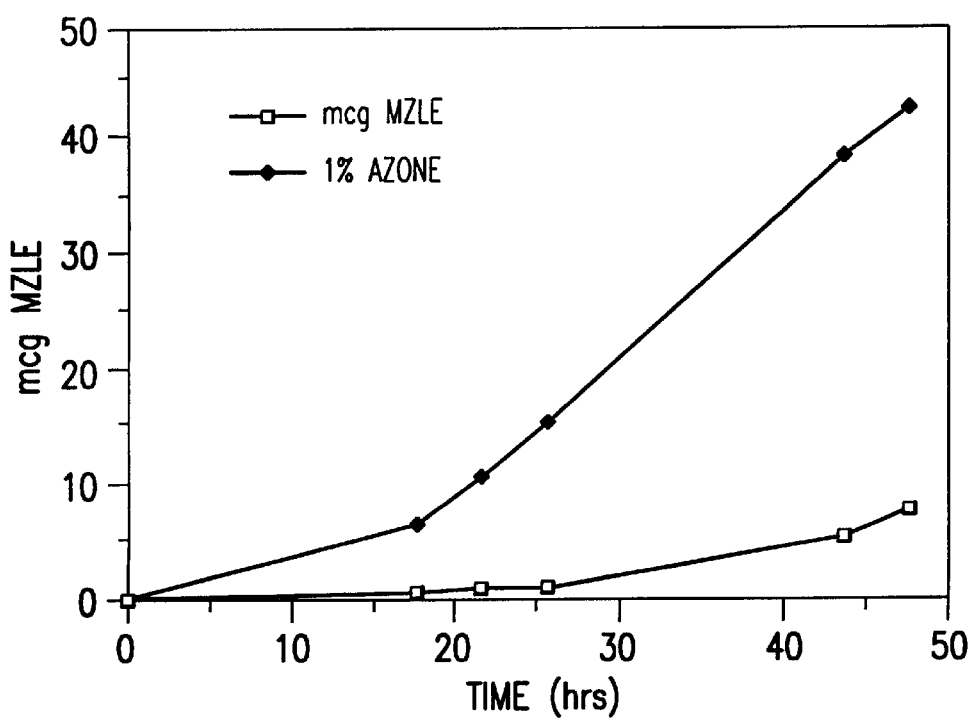
FIG. 4 is a plot of MZLE penetration through female Caucasian skin samples as a function of time and showing the effect of Azone® on penetration.

As shown in FIG. 3, the model compound metronidazole (MZLE) is shown to penetrate the skin from the control (ethanol) solution at a much faster rate than from a solution containing 1% of the penetration prevention agent of Example 1. In contrast, FIG. 4 shows that when 1-N-dodecylazacycloheptan-2-one (Azone®), a known penetration enhancer, replaces the compound of Example 1, the rate of penetration into the receptor solution is greatly increased. This shows that the compound of Example 1 decreases the penetration of metronidazole as compared with control, wherein no other compound is added.

While particular embodiments of the invention have been described, it will be understood of course that the invention is not limited thereto since many obvious modifications can be made; and it is intended to include within this invention any such modifications as will fall within the scope of the appended claims.

What is claimed is:

1. A method for decreasing the percutaneous absorption of toxic chemicals through the skin of a mammal in need of said decreasing which comprises applying to the stratum corneum of the skin of said mammal an effective amount to decrease the percutaneous absorption of toxic chemicals of a compound having the formula:

$$\begin{array}{c} W_2 \\ \parallel \\ W_1 \diagup C \diagdown \qquad W_3 \\ \qquad \diagdown \quad \parallel \\ \qquad N-C-R \\ \diagup \\ (CH_2)_n \end{array}$$

wherein $W_1$, $W_2$ and $W_3$ are each divalent oxygen, n is 2 and R is a straight chain alkyl radical containing 6 to 20 carbon atoms;

wherein when the skin of said mammal is exposed to said toxic chemicals, the penetration of said toxic chemicals through the skin is decreased.

2. The method of claim 1, wherein said compound is N-dodecanoyl-2-oxazolidione.

3. A method for increasing the stability of lipid bilayers in mammalian skin in order to decrease passage of bioactive agents through the skin of a mammal in need of said decreasing, said method comprising the step of applying to the stratum corneum of the skin of said mammal an amount effective to decrease passage of bioactive agents through said lipid bilayers of a lipid-bilayer-stability-increasing compound having the formula:

$$\begin{array}{c} W_2 \\ \parallel \\ W_1 \diagup C \diagdown \qquad W_3 \\ \qquad \diagdown \quad \parallel \\ \qquad N-C-R \\ \diagup \\ (CH_2)_n \end{array}$$

wherein $W_1$, $W_2$ and $W_3$ are each divalent oxygen, n is 2 and R is a straight chain alkyl radical containing 6 to 20 carbon atoms;

wherein when the skin of said mammal is exposed to bioactive agents, the passage of said bioactive agents through the skin is decreased.

4. The method of claim 3, wherein said stability-increasing compound is N-dodecanoyl-2-oxazolidinone.

* * * * *